United States Patent
Törmälä et al.

[11] Patent Number: 6,015,410
[45] Date of Patent: *Jan. 18, 2000

[54] BIOABSORBABLE SURGICAL IMPLANTS FOR ENDOSCOPIC SOFT TISSUE SUSPENSION PROCEDURE

[75] Inventors: Pertti Törmälä ; Markku Tamminmäki; Pertti Helevirta, all of Tampere, Finland; Dennis M. Nigro, Encinitas, Calif.

[73] Assignee: Bionx Implants Oy, Tampere, Finland

[*] Notice: This patent issued on a continued prosecution application filed under 37 CFR 1.53(d), and is subject to the twenty year patent term provisions of 35 U.S.C. 154(a)(2).

[21] Appl. No.: 08/997,458

[22] Filed: Dec. 23, 1997

[51] Int. Cl.$^7$ .................................................. A61B 17/00
[52] U.S. Cl. ................................................ 606/73
[58] Field of Search ............................ 606/232, 72, 73, 606/75, 151, 65–67; 411/34–38, 59–61, 43, 511; 52/512

[56] References Cited

U.S. PATENT DOCUMENTS

| | | | |
|---|---|---|---|
| 4,726,164 | 2/1988 | Reinwall et al. | 52/410 |
| 4,743,257 | 5/1988 | Törmälä et al. | |
| 4,898,186 | 2/1990 | Ikada et al. | |
| 4,968,317 | 11/1990 | Törmälä et al. | |
| 4,988,351 | 1/1991 | Paulos et al. | 606/72 |
| 5,611,814 | 3/1997 | Lorene | |
| 5,634,926 | 6/1997 | Jobe | |
| 5,725,541 | 3/1998 | Anspach, III et al. | 606/232 X |

FOREIGN PATENT DOCUMENTS

| | | |
|---|---|---|
| 0 146 398 | 6/1985 | European Pat. Off. |
| 451932 | 10/1991 | European Pat. Off. ............. 606/73 |
| WO96/21628 | 7/1996 | WIPO |

OTHER PUBLICATIONS

M. Pakkanen, M.D., et al., "Biodegradable Positive Fixation for the Endoscopic Brow Lift" Plastic and Reconstructive Surgery, Nov. 1996, pp. 1087–1091.

S. Vainionpää et al. "Surgical Applications of Biodegradable Polymers in Human Tissues" Prog. Polym. Sci., vol 14, 679–716, 1989.

Primary Examiner—Michael Buiz
Assistant Examiner—Vikki Trinh
Attorney, Agent, or Firm—Kenyon & Kenyon

[57] ABSTRACT

A bioabsorbable surgical implant for use in supporting soft tissue in a superior position in the body is described. The surgical implant includes a shaft that connects the implant to a bone or hard tissue and a head secured to the shaft. The head of the implant has a concave lower surface so that a suture (or sutures) can easily be wound around the shaft below the head and locked to this position by tightening the head against bone or hard tissue and by pushing or turning the shaft into the bone or hard tissue. The connected shaft and head are formed from a resorbable polymer, copolymer, polymer alloy or composite, which maintains a specified strength for a period of time at least equal to a healing period for the patient. Thereafter, the surgical implant is substantially resorbed by the body over a period of time needed for healing. The surgical implant is particularly adapted for use in endoscopic face and/or brow lift surgery and other endoscopic cosmetic, plastic and reconstructive surgical procedures, where sutures are applied for tissue lifting.

7 Claims, 5 Drawing Sheets

BIOABSORBABLE SURGICAL IMPLANTS FOR ENDOSCOPIC SOFT TISSUE SUSPENSION PROCEDURE

BACKGROUND OF THE INVENTION

The invention is generally directed to the use of bioabsorbable suspension devices in connection with plastic surgery and related surgical procedures where sutures are applied for tissue lifting and, in particular, to a new bioabsorbable implant and its use in connection with endoscopic brow and face lift surgery and similar procedures.

Various approaches have been used to shift and hold soft tissue in place during the course of plastic surgery modification of a patient's anatomy. A brow lift procedure is used to eliminate the generally horizontal lines on a patient's forehead at rest, by elevating the top of the patient's brow from the skull and suspending the brow in a superior position for a sufficient period of time so that the soft tissue of the scalp and connective tissue knits in place, leaving the patient with an unlined brow. In the past, invasive surgery using standard surgical cutting tools and open surgical sites using a scalpel have resulted in large entry wounds which tend to create large scars which must be hidden where possible, under the patient's hairline. However, in many cases, the patient's hairline is inadequate as a means for camouflaging the surgical incision and, as a result, such operations were generally not favored due to the complications as well as the large scars which would result.

Today, it is possible to conduct the brow and/or face lift surgery with the use of an endoscope, allowing the physician to make a small incision through which he can extend the necessary tools, view the work area and complete the surgery, all without the need for a large surgical incision. Such endoscopes are similar to arthroscopes utilized in connection with surgery conducted on the knees, shoulders and elbows. In the traditional surgery, the soft tissue of the scalp above the brow is held in place by an outside support. Recently, biostable surgical pins or posts have been put in place in the skull to anchor the soft tissue or sutures holding the soft tissue in place. After a period of time following the completion of the healing process, during which the soft tissue is firmly bonded into its new location, the surgeon must reenter the site, remove the pin or post and then reclose the incision. This procedure increases the risk of infection, as a substantial risk of infection exists each time an incision is made. Furthermore, the patient must return and must again suffer the pain or at least discomfort of further incision, including the risk of anesthesia, whether local or general, as well as the need to have further bandages. In some cases, the metal posts or pins are left in the wearer's skull. However, this may be cosmetically unacceptable and metal implants can cause problems to the patient, in the long term.

In the prior art, it is known to use small bioabsorbable screws, tacks or appliances for fixing of tissues or tissue-lifting sutures, e.g., in face and brow lift surgery. See, e.g., M. Pakkannen et al., Biodegradable Positive Fixation for the Endoscopic Brow Lift, Plastic And Reconstructive Surgery, Vol. 98, No. 6 (Nov. 1996) at 1087–1091, and U.S. Pat. No. 5,611,814, the entire disclosures of both of which are incorporated herein by way of this reference. However, the head of such screws or tacks and the gripping member of such appliances is bulky, making a prominent protrusion on the bone surface. Additionally, the suture(s) must be knotted around the proximal part of the screw or tack, which is a tedious procedure, and the suture knot forms an increment of the protrusion of material on the bone surface. Since the lower surface of the head of such screws or tacks is convex or even (straight), the protrusion of the head is emphasized after knotting of the suture around the shaft of the screw or tack. The head of the screw or tack and knot protrusion on the bone surface can cause a cosmetic disadvantage and may lead to tissue reactions like oedema, swelling or pain during the biodegradation of the screw or tack and/or suture(s). Risks of similar problems are present when using appliances with gripping members.

U.S. Pat. No. 5,634,926, the entire disclosure of which is incorporated herein by reference, describes a bone fixation device, including a post device having an enlarged end portion and a leg portion, which may be slipped into a hole formed in bone. This device may be used for fixation of a suturing element by tying or wrapping the suturing element around the leg portion below the enlarged end.

However, the lower surface of the end portion is even, so that when the suturing element is tied or wrapped around the leg portion below the end portion, the suture loop prevents contact between the lower surface of the end portion and the bone surface. As such, the end portion of that device cannot be pushed tightly against the bone surface and, instead, it forms a protrusion above the bone surface, as can be seen from FIG. 9 of U.S. Pat. No. 5,634,926.

Accordingly, there is the need for an improved surgical implant for supporting soft tissue fixing suture(s) in a specified fixed location, in which the surgeon would only need to once invasively enter the patient's body. It is desirable that the the implant would not cause any cosmetic disturbances or harmful tissue reactions, while suspending the soft tissue or scalp by means of sutures. The implant should have the appropriate structural requirements necessary to retain the soft tissue in place under tension, and to maintain those characteristics for a sufficient time to allow complete heating. In addition, the fixing of suture(s) to the implant should be simple. The implant and the suture(s) should make only a minimal protrusion on the bone surface, and the implant and suture(s) should be absorbed by the body naturally over a period of time, while causing only a minimal tissue reaction so that no further surgical procedure is necessary.

SUMMARY OF THE INVENTION

The invention is generally directed to a surgical implant for fixation of suture(s) used in supporting soft tissue in a superior position in the body. The surgical implant includes a shaft adapted to connect the surgical implant to a bone or hard tissue. The surface of the stem can include ridges, threads, barbs or other projections, which facilitate the locking of the stem into a (drill) hole in bone or soft tissue.

The proximal end of the implant is its head. The head resembles the cap of a mushroom, with a convex outer surface and a concave lower surface, from which the shaft emerges. This special design of the head allows the surgeon to wind the end part(s) of face lifting suture(s) around the shaft, just below the head, before pushing or turning the implant shaft tightly into a (drill) hole in bone or hard tissue, so that the head is located tightly on the bone or hard tissue. When the implant stem is locked in this way tightly into the drill hole, and the suture is wound into the concave space around the shaft below the head, the strong frictional forces retain the suture locked around the shaft and no knotting is needed.

A bioabsorbable polymer, copolymer, polymer blend or composite is used to form the implant, so that it maintains a specified percentage of its strength within the bone or hard tissue for a period of time at least equal to the healing period. The wound suture grips the soft tissue so as to retain the soft tissue in a superior position for a period of time at least equal to the healing period. Thereafter, the implant and the suture (s) are substantially resorbed by the body over a period of time. As a result, in a single procedure, the implant and the suture may be inserted, enabling movement of the soft tissue to a superior position, and the soft tissue's superior position can be retained for a healing period, all without the need for a second procedure to remove the implant or suture and avoiding the permanent presence of implants or sutures in the body.

Under the invention, an incision is made through the skin and soft tissue to a supporting structure (bone), a hole is drilled (or optionally tapped) in the supporting structure, a resorbable surgical implant having a shaft and a head is pushed or screwed partially into the hole in the supporting structure. Next, the soft tissue is biased toward the superior position using suture(s), and the soft tissue is draped in place by winding the free ends(s) of the suture(s) around the proximal part of the implant shaft, just below the lower concave surface of the head. The shaft is then pushed or screwed tightly into the hole in the supporting structure (e.g., bone), so that the tissue lifting suture(s) are tightly fixed below the head of the implant. The incision is closed and the implant and suture(s) hold the soft tissue in the superior position for at least a period of time equal to a healing period. Thereafter, over a period of time, the implant and suture(s) are absorbed by the body so that the superior position of the soft tissue is permanently retained, without the need for further procedures or the continuing presence of the implant and suture.

Another object of the invention is to provide an improved bioabsorbable surgical implant for endoscopic brow lift surgery. A further object of the invention is to provide improved bioabsorbable surgical implants for use, in pairs, in connection with endoscopic brow lift surgery, whereby minute incisions in a single procedure can cure brow furrows, without the need for further procedures to remove implants, external support and avoiding the permanent presence of implants in the body.

A further object of the invention is to provide an improved bioabsorbable surgical implant for use in plastic surgery for anchoring the brow lifting suture(s) in a new, more superior position, as in an endoscopic lift. A further object of the invention is to provide an improved bioabsorbable surgical implant for use in anchoring the face (as in a face lift) in a more youthfull position. A further object of the invention is to provide an improved bioabsorbable surgical implant for suspending with suture(s) any soft tissue such as skin, muscle and/or fascia, from a bony prominence, as in reconstructive surgery.

A further object of the invention is to provide an improved bioabsorbable surgical implant for use in scalp surgery (as in scalp reduction for hair loss) to anchor the scalp lifting suture(s) and minimize scars by diverting tension from wound edges. A further object of the invention is to provide an improved bioabsorbable surgical implant for use in fixing of suture(s) supporting soft tissue, so as to minimize scar formation by diverting tension from wound edges and giving a less substantial scar formation and a cleaner healing of the skin tissue. A further object of the invention is to provide an improved bioabsorbable surgical implant for maintaining, by means of suture(s), soft tissue in a superior position (under tension) for a sufficient period time for the soft tissue to retain its superior position without support, and thereafter for the surgical implant to be absorbed by the body.

A further object of the invention is to provide an improved operating procedure for endoscopically lifting a patient's brow, utilizing an absorbable surgical implant which fixes tissue lifting suture(s) to the skull and, after the brow has rehealed in a superior position, is absorbed completely by the body. Still other objects and advantages of the invention will be apparent from the specification.

BRIEF DESCRIPTION OF THE DRAWINGS

For a fuller understanding of the invention, reference is made to the following description taken in connection with the accompanying drawings, in which.

DETAILED DESCRIPTION OF THE PREFERRED EMBODIMENTS

Figure 1:
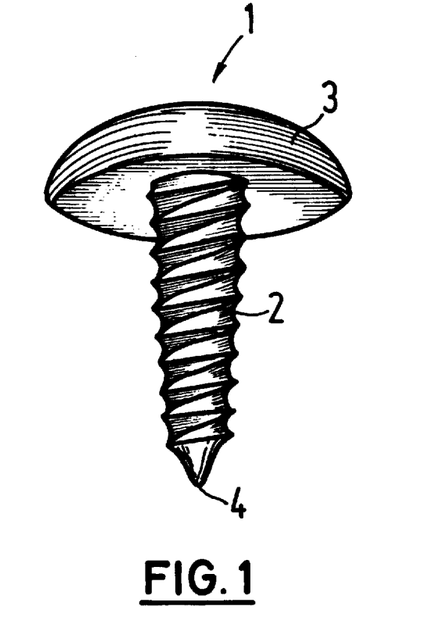
FIG. 1 is an enlarged perspective view of a bioabsorbable surgical implant, constructed and arranged in accordance with a preferred embodiment of the invention.
Figure 2:
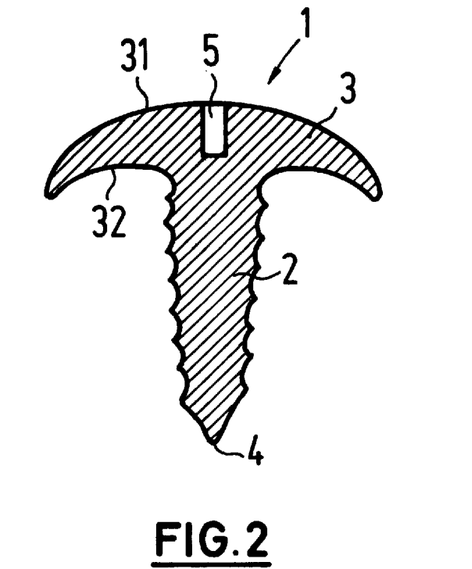
FIG. 2 is a longitudinal cross-sectional view of the implant of FIG. 1.

Reference is made to FIGS. 1 and 2, wherein a bioabsorbable surgical implant, generally indicated as 1, constructed in accordance with a preferred embodiment of the invention is depicted. Implant 1 includes a shaft 2 and a head 3. Shaft 2 can have protrusions, like threads, ridges, barbs, etc. about its circumference. Shaft 2 and head 3 have a generally round cross-section. Tip 4 of shaft 2 may be tapered to facilitate its insertion into a drill hole in bone.

Figure 3:
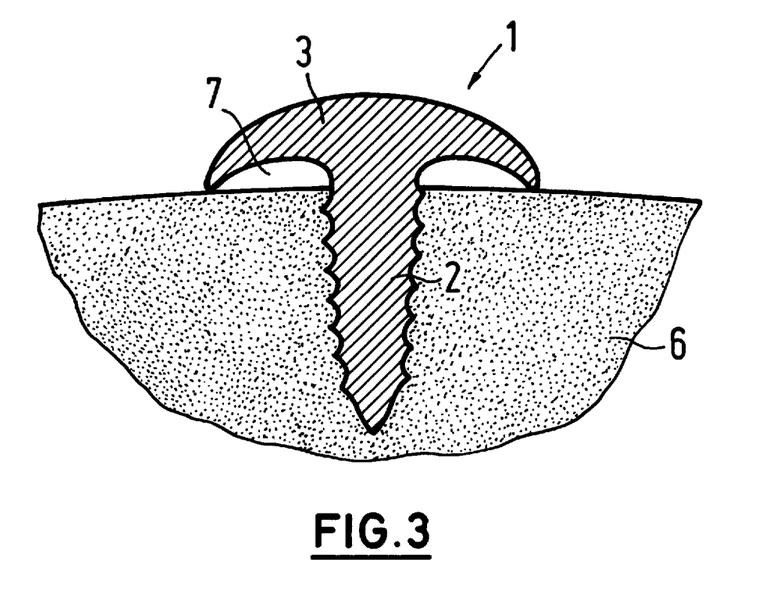
FIG. 3 is a longitudinal cross-sectional view of the implant of FIG. 2, shown as screwed tightly into a tapped drill hole in bone.

The head 3 is relatively thin and it has an upper convex surface 31 and a lower concave surface 32 (FIG. 2), so that when the implant has been screwed tightly into a drill hole in bone 6 (see FIG. 3), the rim of the head can make contact with the bone surface and a small ringlike space 7 is formed between the head 3 and bone 6. The wound suture later will be tightened during implant insertion into the space 7.

Figure 4A:
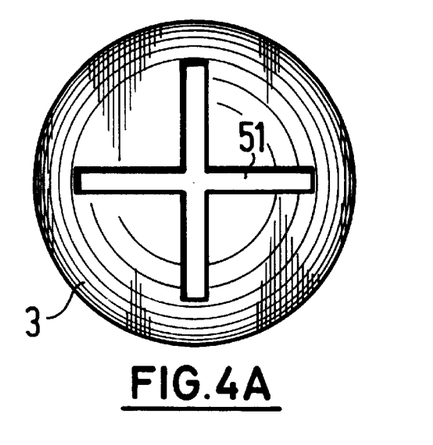
FIG. 4A is an upper view of an implant of the invention, in the direction of the long axis of the shaft, showing the upper side of the head with a cross-like groove for receiving an insertion device.
Figure 4B:
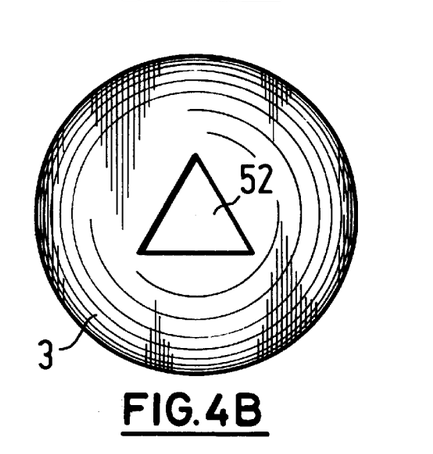
FIG. 4B is an upper view of an implant of the invention, in the direction of the long axis of the shaft, showing the upper side of the head with a triangular groove for receiving an insertion device.
Figure 4C:
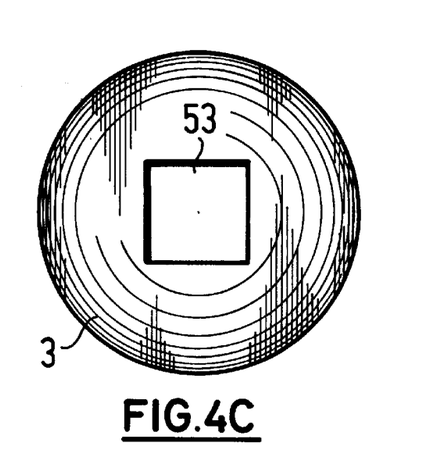
FIG. 4C is an upper view of an implant of the invention, in the direction of the long axis of the shaft, showing the upper side of the head with a quadrangular groove for receiving an insertion device.
Figure 4D:
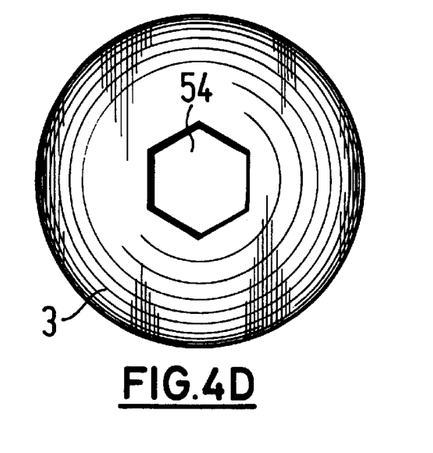
FIG. 4D is an upper view of an implant of the invention, in the direction of the long axis of the shaft, showing the upper side of the head with a hexagonal groove for receiving an insertion device.
Figure 4E:
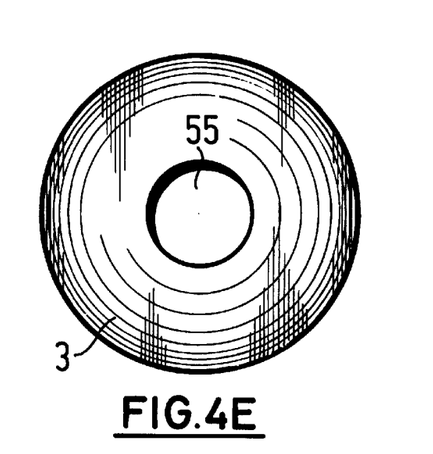
FIG. 4E is an upper view of an implant of the invention, in the direction of the long axis of the shaft, showing the upper side of the head with a circular groove for receiving an insertion device.

The head 3 is usually circular in form when examined along the long axis of shaft 2. The head 3 includes a gripping element, groove or notch 5 (see FIG. 2) for gripping the tip of an insertion device. FIGS. 4A–4E show some typical gripping elements. FIG. 4A shows a cross-like notch 51, FIG. 4B a triangular notch 52, FIG. 4C a quadrangular notch 53, FIG. 4D a hexagonal notch 54 and FIG. 4E a circular notch 55. The notch geometries 4A–4D can be used in connection with a screw-driver installation instrument or with a pushing-type (bayonet-like) instrument, and the notch geometry 4E with a pushing-type instrument.

In a preferred embodiment of the invention, the strength retention time (holding period) of the implant is at least three weeks, preferably four to eight weeks and even more preferably at least six weeks. Finally, the material should fully absorb after tissue healing. Different optimum periods and percentages of holding power will be necessary depending upon the nature of the surgery contemplated.

By varying the composition of the materials used to make the implant, the absorption of the implant can be affected so as to either enhance or delay bioabsorption.

Reference is next made to FIGS. 5A–5G and 6 in which a procedure for endoscopic brow lift surgery is generally depicted. The drawings are only schematic in nature and are not intended to accurately reproduce the underlying structures, blood vessels, nerve fibers and tissue structure found at or about the brow and skull of an actual patient.

Figure 5A:
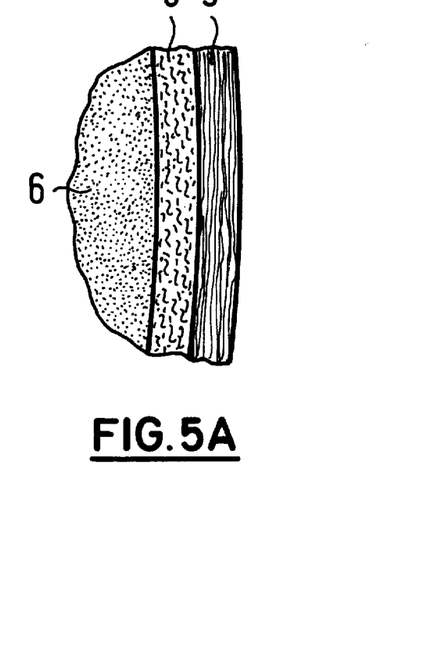
FIG. 5A is an enlarged partial cross-sectional view, taken along a vertical line, showing the brow and skull region to receive the implant of the invention, prior to the insertion procedure.

FIG. 5A shows the brow region of the patient in side cross-section, generally showing a brow prior to an endoscopic brow lift surgical procedure. The figure shows a skull bone 6, soft tissue 8 and scalp 9.

Figure 5B:
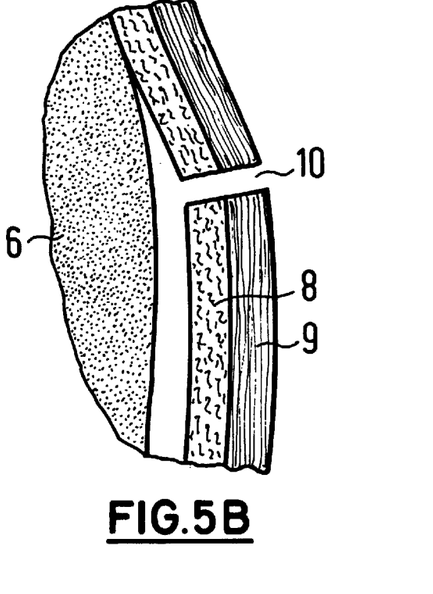
FIG. 5B is a cross-section similar to the cross-section of FIG. 5A, following creation of an endoscoping work incision and separation of the soft tissue of the scalp and brow from the skull.

In FIG. 5B, a small incision 10 is made above the hairline and the endoscope (not shown) is inserted. The endoscope is a well known tool for viewing and controlling delicate surgery performed through a small slit, rather than a large incision in which the field of activity is exposed. The soft tissue 8 and scalp 9 are elevated using tools and through the visual control that is available as a result of the endoscope's use. This elevation can also be performed conventionally.

Figure 5C:
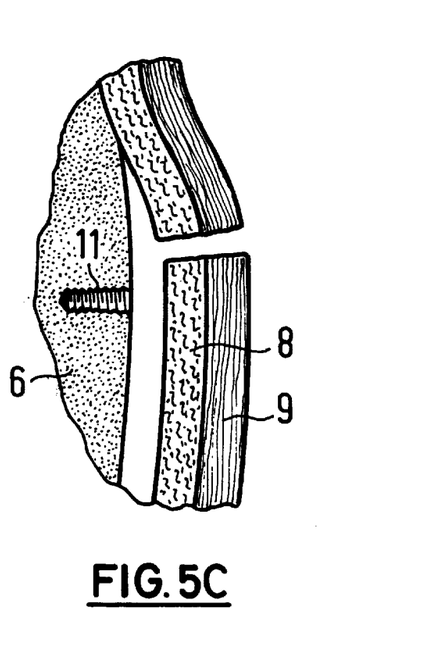
FIG. 5C is a cross-section similar to the cross-section of FIG. 5C, following the drilling and optional tapping of a small hole in the skull.

FIG. 5C shows how a small hole 11 is then drilled into the skull. The hole 11 can optionally be threaded (as in FIG. 5C).

Figure 5D:
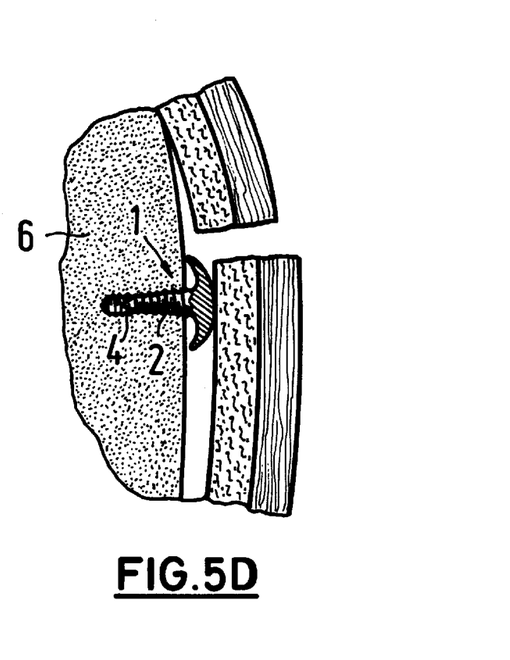
FIG. 5D is a cross-section similar to the cross-section of FIG. 5C, following the screwing of a bioabsorbable implant partially into the drill hole.

FIG. 5D shows how a bioabsorbable implant 1 has then been inserted into the drill hole. Leading end 4 of shaft 3 has been placed in the opening of the hole and the implant has been screwed in partially.

Figure 5E:
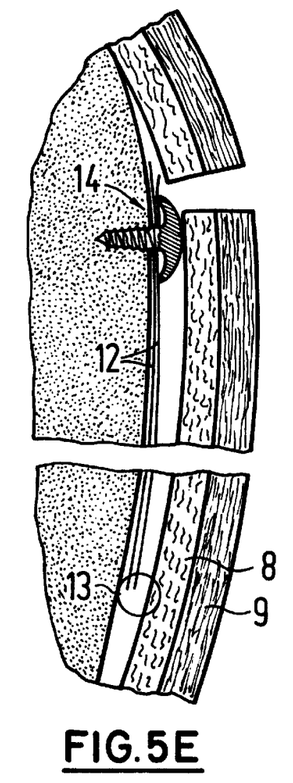
FIG. 5E is a cross-section similar to the cross-section of FIG. 5D, following the pulling up of the soft tissue of the brow and scalp with a suture loop sewed through the soft tissue, which suture is then wound around the shaft of the implant.
Figure 5F:
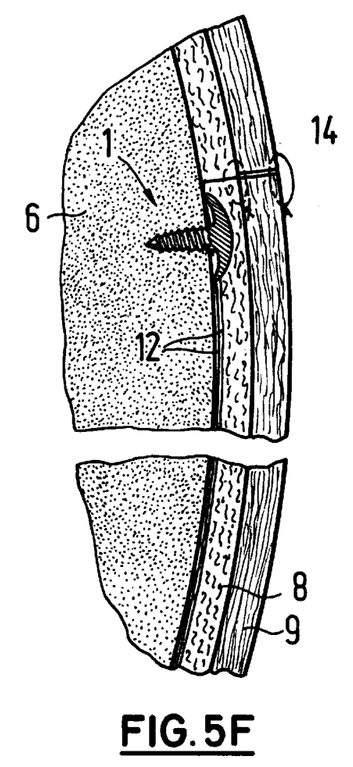
FIG. 5F is a cross-section similar to the cross-section of FIG. 5E, showing the result of operation of the brow lifting, where the lifting suture is fixed tightly below the head of the implant which has been screwed tightly into a drill hole in bone.

FIG. 5E shows how a brow lifting suture loop has been fixed into the soft tissue 8 by sewing through soft tissue in a circled area 13. The free ends 14 of the suture have been stretched upward and tightened to lift the soft tissue and scalp in a proper way (to remove the furrows in scalp). Thereafter, the free ends of the tightened suture are wound once or several times around the shaft of the implant just below the head (see FIG. 5E). Now, the implant can be screwed in until the appropriate tightening of wound suture ends between the head of implant and the surface of bone is achieved, as is seen schematically in FIG. 5F. FIG. 5F also shows how the incision has been closed with additional sutures 14, whereafter the bioabsorbable implant makes only a small, cosmetically acceptable and safe protrusion on the surface of bone below soft tissue 8 and scalp 9.

Figure 6:
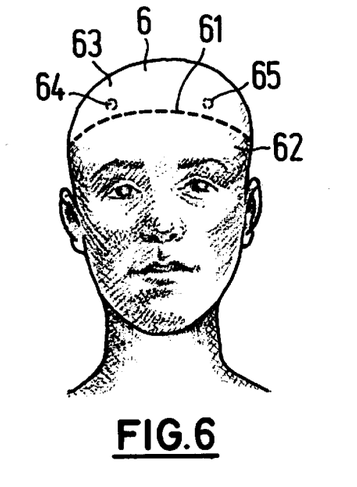
FIG. 6 is a front elevational view of a patient's head, showing the outward manifestation of the surgical procedure following its completion.
Figure 7A:
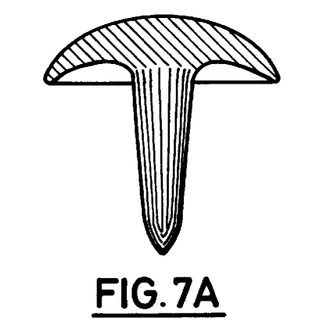
FIG. 7A–7E are enlarged longitudinal cross-sectional views of the implants of the invention showing some preferred directions of molecular orientation and/or reinforcing elements.
Figure 7B:
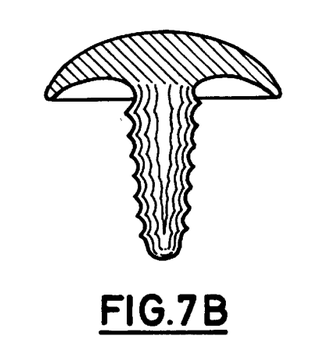
Figure 7C:
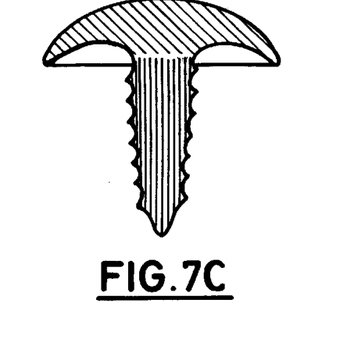
Figure 7D:
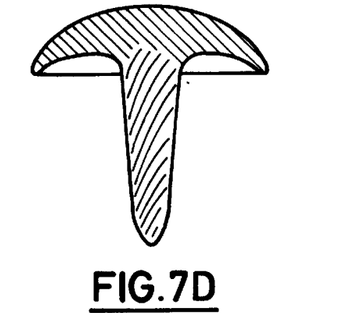
Figure 7E:
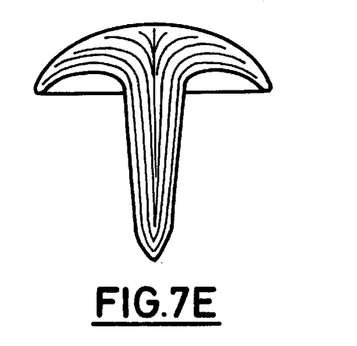

Referring to FIG. 6, in the hair-covered portion 63 of the skull 6 of a patient, the bioabsorbable implants are located below the skin and soft tissue in locations 64 and 65. The implants are difficult to palpate because of the unique thin, convex-concave structure of the head of the implant.

Figure 5G:
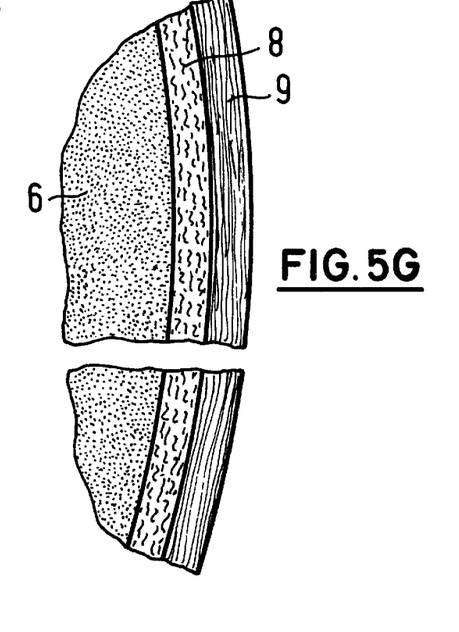
FIG. 5G is a cross-sectional view similar to FIG. 5F, after the surgical implant and suture have been absorbed by the body.

Finally, FIG. 5G shows the last stage of the procedure, following the period during which the scalp and other soft tissue has been held in the new, superior position against the skull 6 for a sufficient healing period, i.e., generally for at least three weeks, preferably four to six weeks and even more preferably for at least six weeks. Thereafter, as the bioabsorbable implant 1 and suture(s) 12 are absorbed after an absorption period (preferably under 3 years), the bone mass drilled out in hole 11 can grow back, leaving no evidence of the surgical procedure other than the desired smooth outer brow surface. Scalp 9 and soft tissue 8 heal and knit firmly with the bony surface of skull 6 along the brow in the new, superior position, which is enabled and maintained by the bioabsorbable implant and suture(s) during their period of residence within the brow region.

Reference is next made to FIG. 6, wherein a frontal view of a patient after undergoing the endoscopic brow lift surgery in accordance with the preferred embodiment described above, including use of bioabsorbable implants 1 and sutures 12, is depicted. As seen in FIG. 6, the skull 6 includes the hairline 61 separating the exposed brow portion 62 from the hair covered portion 63. In the hair covered portion 63, the locations 64 and 65 of bioabsorbable implants below the scalp and soft tissue are practically invisible and unidentifiable on the skin surface, because of the novel convex-concave structure of the head of the implant and as a result of the non-knotted fixation of the sutures. Therefore, the operation can even be performed on individuals with limited or no hair in view of the tiny incision initially made and the practical invisibility of the implant locations 64 and 65.

The surgical implant 1 and variations thereof may be modified and constructed in various sizes and shapes, as required by the parameters and needs of varying types of surgical procedures. In connection with the endoscopic brow lift surgery, in a preferred embodiment the entire surgical implant 1 of the invention has a length of about 6 millimeters, of which 4 millimeters represents the shaft 2 and 2 millimeters represents the height of the head portion 3, which has a diameter of 1–2 millimeters. Smaller or larger dimensions may be made depending upon the varying needs, strengths and positions in which surgical implants 1 are utilized. Surgical implants disclosed and described may be utilized in varying ways and in varying procedures to provide an improved method for retaining soft tissue, skin and scalp at superior positions in connection with cosmetic, plastic and reconstructive surgery. In addition, particularly in connection with operations which traditionally leave substantial and large scars, the surgical implants disclosed herein may be used to relieve and reduce tension at the major incision areas so as to aid in more effective healing of the incision with reduced scar tissue formation.

The bioabsorbable implants of this invention can be manufactured of bioabsorbable polymers, copolymers or polymer mixtures or alloys with melt molding methods known in the prior art. It is also possible to use the techniques of U.S. Pat. No. 4,743,257, the entire disclosure of which is incorporated herein by reference, to mold in a compression or injection mold absorbable fibers and binding polymers together, to create a fiber-reinforced or especially a self-reinforced structure for the implant. The implants of this invention can be molded in a single compression molding cycle, or the protrusions can be machined on the surface of an implant after the molding cycle.

An oriented or self-reinforced structure for the implants can also be created during extrusion or injection molding of absorbable polymeric melts through a suitable die or into a suitable mold at high speed and pressure. When cooling occurs, the flow orientation of the melt remains in the solid material as an oriented or self-reinforcing structure. In an advantageous embodiment, the mold can have the form of the implant, but it is also possible to manufacture the implants of the invention by machining (and/or optionally heating) injection-molded or extruded semifinished products. It is advantageous to make the implants of melt-molded, solid state drawn or compressed, bioabsorbable polymeric materials, which are described, e.g., in U.S. Pat. Nos. 4,968,317 and 4,898,186, the entire disclosures of which are incorporated herein by way of this reference.

The reinforcing fibers of the implant can also be ceramic fibers, like bioabsorbable hydroxyapatite or bioactive glass fibers. Such bioabsorbable, ceramic fiber reinforced materials are described, e.g., in published European Patent Application No. 0146398 and in WO/96/21628, the entire disclosures of which are incorporated herein by way of this reference.

The oriented or self-reinforced or otherwise fiber-reinforced implants of this invention can be manufactured by molding the reinforcement fiber-polymer matrix to the final product in a mold, whose mold cavity has the form of the final implant product, or the final form of the implant can be machined mechanically (and/or optionally using heat) on a preform, such as a melt-molded and solid-state drawn rod, as is described, e.g., in U.S. Pat. No. 4,968,317.

FIG. 7 presents some advantageous embodiments of the implant of this invention, and demonstrates the direction of the orientation and/or reinforcing elements in those implants. According to FIG. 7A, the molecular orientation and/or reinforcing elements are mainly oriented in the direction of the long axis of the shaft of the implant. The reinforcement elements and/or orientation also may extend into any protrusions or ridges of the implant (see FIGS. 7B–7C). The reinforcement elements also can turn spirally around the long axis of the implant (FIG. 7D). Alternatively, the reinforcement elements can form 3-dimensional structure(s) inside of the implant. In some advantageous embodiments the reinforcing elements extend into the head of implant (e.g. FIG. 7E). Other, different orientations for reinforcement elements in implants, which are known from composite technology, can be applied to the present invention.

As a general feature of the orientation, fiber-reinforcement or self-reinforcement of the implants of this invention, many of the reinforcing elements are oriented in such a way that they can carry effectively the different external loads (such as tensile, bending and shear loads) that are directed to the implant as used.

According to an advantageous embodiment of the invention, the implant, or a bioabsorbable polymeric coating layer on its surface, may contain one or more bioactive substances, such as antibiotics, chemotherapeutic substances, angiogenic growth factors, substances accelerating the healing of the wound, growth hormones and the like. Such bioactive implants are especially advantageous in surgical use, because they chemically contribute to the healing of the operated tissue(s), in addition to providing mechanical support.

The oriented and/or reinforced materials of the implants typically have tensile strengths of 100–2000 MPa, bending strengths of 100–600 MPa and shear strengths of 80–400 MPa. Additionally, they are usually stiff and tough. These mechanical properties are superior to those of non-reinforced or non-oriented absorbable polymers, which typically show strengths between 40 and 100 MPa and are additionally either very flexible or brittle. See, e.g, S. Vainionpää, P. Rokkanen and P. Tormnld, "Surgical Applications of Biodegradable Polymers in Human Tissues", Progr. Polym. Sci., Vol. 14, (1989) at 679–716, the full disclosure of which is incorporated herein by way of this reference.

The implants of the present invention may be sterilized by any of the well known sterilization techniques, depending on the type of material used in manufacturing of the implant. Suitable sterilization techniques include heat sterilization, radiation sterilization, such as cobalt 60 irradiation or electron beams, ethylene oxide sterilization, and the like.

It will thus be seen that the objects set forth above, among those made apparent from the preceding description, are efficiently attained and, since certain changes may be made in the above construction without departing from the spirit and scope of the invention, it is intended that all matter contained in the above description or shown in the accompanying drawings shall be interpreted as illustrative and not in a limiting sense.

What is claimed is:

1. A bioabsorbable surgical implant for use in combination with sutures in supporting soft tissue in a position in a body, the surgical implant comprising:
   a shaft having a distal end and a proximal end; and
   a head having a convex outer surface and a continuous concave lower surface extending from said proximal end of said shaft to an edge of said convex outer surface, said proximal end of said shaft being integrally to said continuous concave lower surface of said head.

2. A bioabsorbable surgical implant of claim 1, wherein the shaft contains one or more protrusions.

3. The bioabsorbable surgical implant of claim 1, wherein the protrusions are threads, barbs or ridges.

4. A bioabsorbable surgical implant of claim 2, wherein the outer surface of the head contains a gripping element.

5. A bioabsorbable surgical implant of claim 4, wherein the gripping element is a cruciform, triangular, quadrangular, hexagonal or circular notch.

6. A surgical procedure for supporting soft tissue in an improved position in a body using a bioabsorbable surgical implant of claim 1, an endoscope, an inserting device, and one or more sutures, the procedure comprising;

making a surgical opening proximate to soft tissue to be moved, skin and bone;

inserting the endoscope into the surgical opening for viewing surgical activity;

separating the soft tissue and skin from the bone;

drilling a hole in the bone proximate the soft tissue to be moved;

inserting the bioabsorbale surgical implant of claim 1 partially into the hole;

looping a suture having two free ends through the soft tissue and lifting the soft tissue by tightening the free ends of the suture;

winding the free ends of the suture around the proximal part of the shaft of the implant, just below its head;

inserting the implant into the drill hole with an inserting device, so that the head of the implant tightens against the bone surface and locks the wound suture below the implant head and the suture retains the soft tissue under tension in the desired improved position; and     closing the surgical opening;

7. The procedure of claim 6, wherein the soft tissue and skin being moved is a portion of a brow.

* * * * *

UNITED STATES PATENT AND TRADEMARK OFFICE
CERTIFICATE OF CORRECTION

PATENT NO. : 6,015,410
DATED : January 18, 2000
INVENTOR(S) : Törmälä, et al.

It is certified that error appears in the above-identified patent and that said Letters Patent is hereby corrected as shown below:

Column 8,
Line 33, "Vainionpää" should be -- Vainionpää
Line 33, "Tormnld " should be -- Törmälä --;
Line 60, "integrilly" should be -- integrally connected --;

Column 9,
Line 16 "bioabsorbale" should be -- bioabsorbable --;

Signed and Sealed this

Twenty first Day of August, 2001

Attest:

NICHOLAS P. GODICI
Attesting Officer    Acting Director of the United States Patent and Trademark Office